(12) United States Patent
Pettigrew et al.

(10) Patent No.: US 8,784,641 B2
(45) Date of Patent: Jul. 22, 2014

(54) METHOD AND APPARATUS FOR DETECTING A LIPOPHILIC ANALYTE OF INTEREST IN A SAMPLE

(75) Inventors: David M. Pettigrew, Huntingdon (GB); Stuart P. Hendry, Royston (GB); Peter G. Laitenberger, Cambridge (GB)

(73) Assignee: Sphere Medical Limited, Cambridgeshire (GB)

( * ) Notice: Subject to any disclaimer, the term of this patent is extended or adjusted under 35 U.S.C. 154(b) by 121 days.

(21) Appl. No.: 13/499,732

(22) PCT Filed: Oct. 11, 2010

(86) PCT No.: PCT/GB2010/051703
§ 371 (c)(1),
(2), (4) Date: Jul. 6, 2012

(87) PCT Pub. No.: WO2011/042757
PCT Pub. Date: Apr. 14, 2011

(65) Prior Publication Data
US 2012/0267259 A1 Oct. 25, 2012

(30) Foreign Application Priority Data
Oct. 9, 2009 (GB) .................................. 0917735.3

(51) Int. Cl.
*G01N 27/49* (2006.01)
(52) U.S. Cl.
USPC .......................................... 205/782; 204/402
(58) Field of Classification Search
CPC ............................................... G01N 33/48714
USPC ...................... 204/403.01–411; 205/782, 778
See application file for complete search history.

(56) References Cited

U.S. PATENT DOCUMENTS

| 5,906,742 A | 5/1999 | Wang et al. |
| 6,831,733 B2 | 12/2004 | Petterson et al. |
| 7,247,484 B2 | 7/2007 | Wu et al. |

FOREIGN PATENT DOCUMENTS

| WO | WO 2005/048126 A2 | 11/2004 |
| WO | WO 2010/017151 A1 | 2/2010 |

OTHER PUBLICATIONS

Cohen et al.; Quantitative measurement of propofol and in main glucuroconjugate metabolites in human plasma using solid phase extraction-liquid chromatography-tandem mass spectrometry; J Chromatogr B Analyt Technol Biomed Life Sci; 854(1-2); pp. 165-172; Jul. 2007.
Dawidowicz et al.; The advantages of cell lysis before blood sample preparation by extraction for HPLC propofol analysis; Biomed Chromatogr; 14(7); pp. 493-497; Nov. 2000.
Pallagi et al.; Mechanism of the Gibbs reaction. Part 4.1 Indophenol formation via n-chlorobenzoquinone imine radical anions .; The Journal of Organic Chemistry; 64(18); pp. 6530-6540; Aug. 1999.
Svobodová et al.; Colour reaction of phenols with the gibbs reagent. The reaction mechanism and decomposition and stabilisation of the reagent; Microchimica Acta; 67; pp. 251-264; May 1977.

(Continued)

Primary Examiner — J. Christopher Ball
(74) Attorney, Agent, or Firm — Shay Glenn LLP

(57) ABSTRACT

Disclosed is a method and apparatus for detecting the concentration of a lipophilic analyte of interest in a complex sample matrix. The method comprises extracting the analyte of interest from said sample into an organic solvent comprising a dissolved electrolyte; providing a free radical species, preferably a free oxygen radical species, in said organic solvent; reacting the analyte of interest with said free radical species; and performing a measurement to detect the concentration of the free radical-reacted analyte reaction product.

14 Claims, 5 Drawing Sheets

(56) References Cited

OTHER PUBLICATIONS

Svobodová et al.; The colour reaction of phenols with the Gibbs reagent; Microchimica Acta; 70(II/3-4); pp. 197-211; May 1978.

Ainashef et al.; Electrochemical Generation of Superoxide in Room-Temperature Ionic Liquids; Electrochemical and Solid-State Letters; 4(11):D16-D18; Nov. 2001.

Araki et al.; Antioxidative properties of probucol estimated by the reactivity with superoxide and by electrochemical oxidation; Chem Pharm Bull (Tokyo); 49(8):943-7; Aug. 2001.

Araki et al.; The mechanism of reaction of ebselen with superoxide in aprotic solvents as examined by cyclic voltammetry and ESR; Chem Pharm Bull (Tokyo); 49(5):541-5; May 2001.

Barr et al.; Propofol dosing regimens for ICU sedation based upon an integrated pharmacokinetic-pharmacodynamic model; Anesthesiology; 95(2); p. 324-333; Aug. 2001.

Beissenhirtz et al.; Comparing an in vitro electrochemical measurement of superoxide scavenging activity with an in vivo assessment of antioxidant potential in Chinese tonifying herbs; Phytother Res.; 18(2):149-53; Feb. 2004.

Beissenhirtz et al.; Immobilized Cytochrome c Sensor in Organic/Aqueous Media for the Characterization of Hydrophilic and Hydrophobic Antioxidants; Electroanalysis; vol. 15, Issue 18, pp. 1425-1435, Oct. 2003.

Campanella et al.; Superoxide dismutase biosensors working in non-aqueous solvent; Fresenius J Anal Chem.; 369(7-8):594-600; Apr. 2001.

Csallany et al.; ?-tocopherol oxidation mediated by superoxide anion (O 2 ? ) I. Reactions in aprotic and protic conditions; Lipids; vol. 27, Issue 3, pp. 195-200; Mar. 1992.

Ezerskis et al.; Electropolymerization of chlorinated phenols on a Pt electrode in alkaline solution Part I: A cyclic voltammetry study; Journal of Applied Electrochemistry; vol. 31; Issue 10; pp. 1117-1124; Oct. 2001.

Ferreira et al.; Electrode passivation caused by polymerization of different phenolic compounds; Electrochimica Acta; vol. 52, Issue 2; pp. 434-442; Oct. 25, 2006.

Gibbs, H.D.; Phenol tests III. The indophenol test; Journal of Biological Chemistry, 72(2); pp. 649-664; 1927 (year of pub. sufficiently earlier than effective US filing date and any foreign priority date).

Gülçin et al.; Determination of in vitro antioxidant and radical scavenging activities of propofol; Chem Pharm Bull (Tokyo); 53(3):281-5; Mar. 2005.

Herath et al.; Electrochemical investigation of superoxide anion scavenging ability of 1,2,3-triketohydrindene hydrate in aprotic solvents; Electrochimica Acta; vol. 51; Issue 14; pp. 2890-2897; Mar. 15, 2006.

Heyne et al.; Investigation of singlet oxygen reactivity towards propofol; Photochem Photobiol Sci; 2(9):939-45; Sep. 2003.

Kohen et al.; Quantification of the overall reactive oxygen species scavenging capacity of biological fluids and tissues; Free Radic Biol Med.; 28(6):871-9; Mar. 15, 2000.

Korotkova et al.; Study of antioxidant properties by voltammetry; Journal of Electroanalytical Chemistry; vol. 518; Issue 1; pp. 55-60; Jan. 11, 2002.

McGaughran et al.; Rapid measurement of blood propofol levels: a proof of concept study; J Clin Monit Comput.; 20(2):109-15; Apr. 2006.

Miniati, Enrico; Assessment of phenolic compounds in biological samples; Ann Ist Super Sanita; 43 (4):362-8; (year of publication is sufficiently earlier than the effective U.S. filing date and any foreign priority date) 2007.

Murphy et al.; The antioxidant potential of propofol (2,6-diisopropylphenol); Br J Anaesth.; 68(6):613-8; Jun. 1992.

Plummer GF; Improved method for the determination of propofol in blood by high-performance liquid chromatography with fluorescence detection; J Chromatogr.; 421(1):171-6; Oct. 9, 1987.

Prieto-Simón et al.; Electrochemical biosensors as a tool for antioxidant capacity assessment; Sensors and Actuators B: Chemical; vol. 129, Issue 1, pp. 459-466; Jan. 29, 2008.

René et al.; Superoxide protonation by weak acids in imidazolium based ionic liquids; J Phys Chem B.; 113(9):2826-31; Mar. 5, 2009.

Shafer et al.; Pharmacokinetics and pharmacodynamics of propofol infusions during general anesthesia; Anesthesiology; 69(3); pp. 348-356; Sep. 1988.

Uebel et al.; Electrochemical determination of 2,6-diisopropylphenol after high-performance liquid chromatography of extracts from serum; J Chromatogr.; 526(1):293-5; Mar. 16, 1990.

Volti et al.; Antioxidant properties of propofol when oxidative stress sleeps with patients; EXCLI Journal; 5:25-32; Apr. 13, 2006.

Pettigrew et al.; U.S. Appl. No. 13/878,815 entitled "Analyte detection method," filed Apr. 11, 2013.

Pettigrew et al.; U.S. Appl. No. 13/878,820 entitled "Analyte extraction apparatus and method," filed Apr. 11, 2013.

Csallany et al.; alfa-tocopherol oxidation mediated by superoxide anion (O2−) I. Reactions in aprotic and protic conditions; Lipids; vol. 27, Issue 3, pp. 195-200; Mar. 1992.

Korotkova et al.; Study of antioxidant properties by voltammetry; Journal of Electroanalytical Chemistry; vol. 518; Issue 1; pp. 56R60; Jan. 11, 2002.

METHOD AND APPARATUS FOR DETECTING A LIPOPHILIC ANALYTE OF INTEREST IN A SAMPLE

FIELD OF THE INVENTION

The present invention relates to a method and apparatus for improving the electrochemical detection of lipophilic molecules in complex media. In particular, the present invention provides a method for selectively measuring the anaesthetic drug Propofol in whole blood.

BACKGROUND OF THE INVENTION

Modern healthcare relies extensively on a range of chemical and biochemical analytical tests on a variety of body fluids to enable diagnosis, therapy and management of disease. Medical and technological advances have considerably expanded the scope of diagnostic testing over the past few decades. Moreover, an increasing understanding of the human body, together with the emergence of developing technologies, such as micro-systems and nanotechnology, are expected to have a profound impact on diagnostic technology.

Increasingly, diagnostic tests in hospitals are carried out at the point-of-care (PoC), in particular in situations where a rapid response is a prime consideration and therapeutic decisions have to be made quickly. Despite recent advances in PoC testing, several compelling needs remain unmet. For example, the detection of small molecules in biological samples is often very challenging, especially when no suitable receptor (e.g. enzyme, antibody, aptamer) with an appropriate specificity exists. The challenge is even greater when the molecule is lipophilic and a large proportion of the analyte is unavailable for analysis due to its association with hydrophobic components of the sample matrix such as cells, lipids and proteins.

The detection of lipophilic molecules in complex media (e.g. blood, plasma, saliva, urine, waste water and their extracts) is often difficult due to the association of the analyte with components of the sample matrix (e.g. plasma proteins and lipid membranes). The free, i.e. unbound, molecule concentration can be in the picomolar range and is often below the sensitivity limits of most commonly used measurement techniques, e.g. electrochemical, optical techniques. For this reason, state of the art methods for lipophilic molecule detection in complex media often involve intensive sample preparation, such as dilution/extraction of the sample into an organic solvent, centrifugation, evaporation and analysis by high pressure liquid chromatography (HPLC). Depending on the specific characteristics of the analyte molecule, post-HPLC column detection of the eluted compound is performed using electrochemical or optical methods such as absorption spectroscopy or fluorescence measurements.

The complex and time-consuming nature of HPLC assays for lipophilic molecules in complex samples mean that they are routinely performed by a very small number of specialist laboratories; for this reason the utility of these assays is rather limited. For example, for many lipophilic drugs, there is a clear need to develop alternative, miniaturised assays. This would enable real-time measurement and clinical intervention at the Point of Care (PoC).

Electrochemical techniques are often more amenable to Point of Care applications than optical ones, due to their lower cost and complexity. However, it is often difficult or impossible to detect lipophilic molecules in aqueous solutions using conventional electrochemical analysis. Reasons for these difficulties include, but are not limited to the fouling of the sensor (and concomitant loss of sensitivity) by surface adsorption of hydrophobic molecules and/or electrochemically generated reaction products; low analyte sensitivity; poor availability of the molecule in solution due to hydrophobic adsorption to components of the sample matrix such as proteins/lipids and a requirement for high oxidation/reduction potentials, thereby increasing the likelihood of other molecules in the sample interfering with the analyte signal.

Phenolic compounds, such as Propofol, are a good illustration of these challenges. Upon oxidation to phenoxy radical intermediates, the molecules can react with each other to form dimers, or can be further oxidised to quinones. Further oxidation cycles generate radical dimers and monomers, which react with each other to form a polymer. Repeated measurement often results in decreased sensitivity, caused by the electrically insulating polymer that builds up on the working electrode. In more complex biological samples, hydrophobic adsorption of components of the sample matrix (e.g. proteins, lipids and cells) to the working electrodes can also result in a severe loss of sensitivity. These problems mean that it is usually very difficult to develop a reliable assay for phenolic compounds, and other lipophilic compounds, in aqueous media.

Non-aqueous solvents are useful for electrochemical detection because the properties of these media can mitigate, or even eliminate, many of the problems described above. For example, the scarcity of protons in aprotic organic media, including Acetonitrile (MeCN), Dimethylsulfoxide (DMSO) and Dimethylformamide (DMF), means that free radical reaction products, such as the phenoxy radical, are much more stable, thereby simplifying the interpretation of the reaction system. Electrode fouling by hydrophobic adsorption is also eliminated through the use of these solvents.

However, not all the problems associated with measurement in water are avoided through the use of organic solvents. For example, some analytes still require high oxidation and reduction potentials for detection, and fouling can still occur, particularly for phenolic compounds such as Propofol. There is therefore a need to improve the reliability of detection and concentration measurement of lipophilic molecules in organic media, especially when the molecule is extracted into the organic media from a complex sample matrix, e.g. is derived from biological samples.

Many lipophilic molecules are potent free radical scavengers. It is possible to study the free radical scavenging ability of these molecules using electrochemical techniques. Most of the investigations presented to date rely on the electrochemical generation of the superoxide anion ($O_2 \cdot^-$). This free radical can be generated in aqueous or organic solvent by the electrochemical reduction of molecular oxygen or by solvation of potassium superoxide ($KO_2$). The reactivity of $O_2 \cdot^-$ differs in water and aprotic organic solvents. In aqueous environments, $O_2 \cdot^-$ —acts as a strong nucleophile and spontaneously reacts with water to give hydro-peroxide and molecular oxygen:

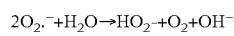

$$2O_2 \cdot^- + H_2O \rightarrow HO_2^- + O_2 + OH^-$$

However, in aprotic media, $O_2 \cdot^-$ is stable for up to 40 minutes and, depending on the species it reacts with, can act as a nucleophile, oxidant, reductant or base. The stability and diverse reactivity of this species in aprotic solvents has been exploited to measure the activity of lipophilic free radical scavengers, such as Probucol, Eblesen and tocopherols (Vitamin E). These assays measured the depletion of superoxide in the presence and absence of these free radical scavengers. A drawback of these assays is that they are not designed for use in clinical environments, e.g. for diagnostic purposes.

SUMMARY OF THE INVENTION

The present invention seeks to provide a method of detecting the concentration of a lipophilic analyte of interest that can be used in clinical environments.

The present invention further seeks to provide an apparatus for detecting the concentration of a lipophilic analyte of interest.

In accordance with a first aspect of the present invention, there is provided a method for detecting the concentration of a lipophilic analyte of interest in a complex sample matrix, the method comprising extracting the analyte of interest from said sample into an organic solvent comprising a dissolved electrolyte; providing a free radical species in said organic solvent; reacting the analyte of interest with said free radical species; and performing a measurement to detect the concentration of the free radical-reacted analyte reaction product.

The present invention is based on the insight that a lipophilic analyte of interest may be extracted from a complex sample matrix, such as a bodily fluid, e.g. blood, into a medium in which free radicals, preferably superoxide radicals, are stable for long enough to perform an indirect concentration measurement of the analyte of interest by measuring the concentration of the reaction product of e.g. a superoxide radical with the lipophilic analyte of interest. This has the advantage that the concentration of the analyte of interest in the complex sample matrix can be readily determined, such that it can be used for the concentration measurement of the lipophilic analyte of interest in clinical environments, such as operating theatres. In addition, the sample preparation required is simpler than that demanded for techniques, such as HPLC, resulting in substantial savings in equipment complexity, financial cost and time of measurement.

Also, the use of an electrochemical rather than an optical detection method provides a route to miniaturisation. The usual problems associated with electrode fouling by adsorbed hydrophobic materials from the complex sample matrix are also avoided by exchange into an organic solvent. This further ensures that the free radical-reacted analyte is much more readily oxidised at lower potentials relative to the unreacted analyte. Therefore, the chance of interference by other oxidisable species is reduced by using lower detection potentials.

In the context of the present invention, a complex sample matrix is a sample from which a direct determination of the concentration of the analyte of interest is not straightforward or even impossible, for instance because the matrix has a complex composition, e.g. a composition having prima facie (unknown) constituents in unknown concentrations, a composition with at least one constituent that interferes with the determination of the concentration of the analyte of interest, a composition including one or more constituents that hamper accurate concentration determination of the analyte of interest, e.g. by fouling the measurement electrodes, and so on.

In a preferred embodiment, a preferred lipophilic analyte of interest is Propofol. Propofol is a short-acting, intravenously administered hypnotic agent. Its uses include the induction and maintenance of general anesthesia, sedation for mechanically ventilated adults, and procedural sedation. Concentration monitoring of Propofol is of critical importance for the safety and welfare of a patient under its administration.

In an embodiment, the organic solvent further comprises a free radical precursor, and wherein the step of providing the free radical species comprises generating said species from the radical precursor. The free radical precursor may be comprised by the dissolved electrolyte. This has the advantage that the free radical species can be generated on demand, thereby maximizing the concentration of the free radical species available for reacting with the lipophilic analyte of interest.

The step of generating the free radical species may comprise holding the organic solvent at a predefined potential for a predefined period of time. This has the advantage of generating the free radical species in a simple and straightforward manner.

In a preferred embodiment, the method further comprises performing a reference measurement prior to said generation step; and detecting the concentration of the lipophilic analyte of interest by subtracting the reference measurement from the measurement. This allows for an accurate determination of the concentration of the lipophilic analyte of interest in the organic solvent, for instance because the signal generated by interfering species also extracted from the complex sample matrix may be filtered out in this manner.

This enhances the selectivity for the analyte of interest by measuring the signal from species that would otherwise interfere with the measurement at the same potential. Specifically, there is a significant improvement over the prior art for the detection of phenols. In this case, the conversion to a free radical-reacted product with different electrochemical properties avoids the problem of phenol radical polymerisation and electrode passivation that is normally associated with conventional electrochemical detection. For example, passivation does not occur when superoxide-reacted phenols are oxidised electrochemically and hence no loss of sensitivity occurs with repeated measurement.

Optionally, the organic solvent including the extracted analyte of interest may be transferred to a radical generation chamber prior to said generating step, and/or the organic solvent comprising the free radical-reacted analyte reaction product may be transferred to an analysis unit prior to performing said measurement.

Suitable organic solvents include aprotic solvents selected from the group consisting of dimethylformamide, acetonitrile and dimethylsulfoxide, as these solvents are particularly suitable for stabilizing the free oxide radical species.

Preferably, the electrolyte cation is selected from the group consisting of a tetra-alkyl ammonium, lithium, sodium, magnesium, sulfonium and cryptate cations.

Preferably, the electrolyte anion is selected from the group consisting of chloride, perchlorate, tetrafluoroborate, hexafluorophosphate, hexafluoroarsenate, trifluoromethanesulfonate, nitrate, aromatic sulfonates and carboxylate anions. The above cations and anions are preferred when using aprotic solvents. It should however be understood that the selection of suitable cations and anions depends on the solvent and the reaction to be carried out.

In an embodiment, the measurement is an electrochemical measurement comprising a potential sweep, said sweep including at least one voltage value matching or exceeding the oxidation or reduction potential of the free radical-reacted analyte reaction product. In this context, it should be appreciated that the voltage exceeding such a potential may be a voltage that is more positive than a positive potential value or more negative than a negative potential value, i.e. has an absolute value that is larger than the absolute value of the oxidation or reduction potential. The selection of such a potential ensures that the reaction between the analyte of interest and the free radical species goes ahead.

In accordance with another aspect of the present invention, there is provided an apparatus for detecting the concentration of a lipophilic analyte of interest, comprising an electrochemical cell for performing a measurement to detect the concentration of a radical-reacted analyte reaction product of a free radical species and an analyte of interest in an organic solvent further comprising an electrolyte dissolved therein, said electrochemical cell comprising a plurality of electrodes; a controller programmed to provide said electrodes with a plurality of voltages including at least one voltage value exceeding the oxidation or reduction potential of the free radical-reacted analyte reaction product; and a signal processor coupled to said electrodes for determining the concentration of the analyte of interest from the signal generated by said electrodes in response to said plurality of voltages.

Such an apparatus has the advantage that the concentration of a lipophilic analyte of interest can be detected in an accurate and fast manner, as previously explained.

In a preferred embodiment, the controller is further programmed to provide said electrodes with a further plurality of voltages defining a reference measurement for detecting the presence of interfering species in the organic solvent, and wherein the signal processor is adapted to determine the concentration of the lipophilic analyte of interest from the difference between the signal generated by said electrodes in response to said plurality of voltages and the signal generated by said electrodes in response to said further plurality of voltages. This further improves the accuracy of the determination of the concentration of the lipophilic analyte of interest as previously explained.

The controller may be further adapted to generate a constant voltage signal over a predetermined time period for generating the free radical species. This has the advantage that the radical species can be generated in situ. The apparatus may have a separate electrochemical cell in fluidic contact with the electrochemical cell in which the voltage sweeps are performed for the generation of the free oxygen radical species. Alternatively, the free radical species may be generated in the electrochemical cell used for the concentration determination of the lipophilic analyte of interest.

BRIEF DESCRIPTION OF THE EMBODIMENTS

Embodiments of the invention are described in more detail and by way of non-limiting examples with reference to the accompanying drawings, wherein FIG. 1 is a flow chart of an embodiment of the method of the present invention;

FIG. 2 schematically depicts an apparatus according to an embodiment of the present invention;

FIG. 3 schematically depicts an apparatus according to another embodiment of the present invention;

DETAILED DESCRIPTION OF THE DRAWINGS

Figure 1:
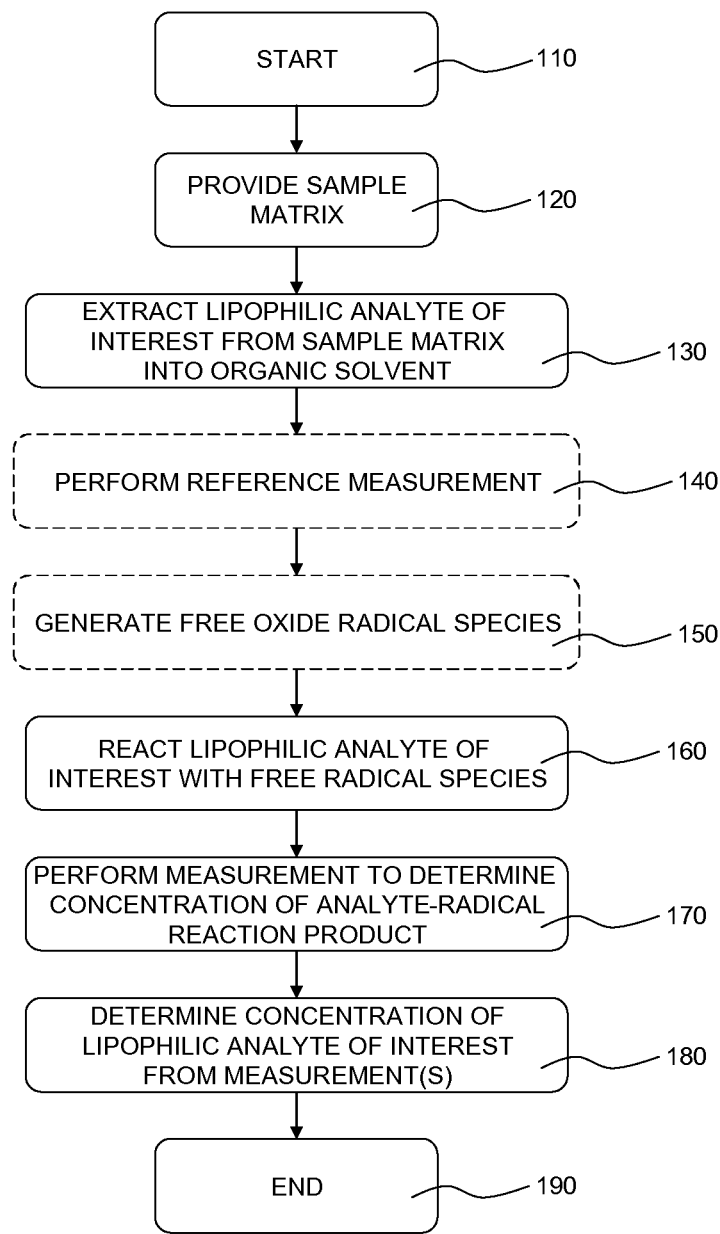

It should be understood that the Figures are merely schematic and are not drawn to scale. It should also be understood that the same reference numerals are used throughout the Figures to indicate the same or similar parts.

FIG. 1 depicts a flowchart of an embodiment of the method 100 of the present invention. The method steps indicated in the dashed boxed in FIG. 1 are optional method steps that may be omitted without departing from the method of the present invention. The present invention will be described with reference to the use of a free oxide radical species as the radical species selected for scavenging the analyte of interest in the method of the present invention. It should however be understood that this is by way of non-limiting example only, and that other free radical species may be used instead without departing from the present invention.

The method 100 starts in step 110 and terminates in step 190. After starting in step 110, the method proceeds with the provision of a complex sample matrix potentially including the lipophilic analyte of interest in step 120. Such a sample may for instance be provided after a medical professional has collected the sample from a patient in any suitable manner. It is expressly noted that this collection step does not form part of the present invention. Alternative sample sources, e.g. samples collected in a non-medical context, are equally feasible.

The method subsequently proceeds to step 130, in which the lipophilic analyte of interest is extracted from the sample matrix and transferred into a suitable organic solvent.

Any suitable extraction method may be used for this purpose. Depending on the method of exchange, e.g. solid phase extraction (SPE), some purification of the analyte relative to any species that may interfere with the measurement is achieved at this stage. Preferred embodiments use aprotic organic solvents including, but not limited to, Dimethylformamide (DMF), Acetonitrile (MeCN) and Dimethylsulfoxide (DMSO). The reason for this preference is that free radical species to be generated are much longer lived in solvents with a low proton activity. However, depending on the reactivity of the analyte molecule of interest to the free-radical being used, it may be possible to use protic solvents, including, but not limited to, methanol. The solvent should also contain a solvated electrolyte, preferably at a concentration of 0.1 M. The electrolyte ensures that the aprotic solvent, which is intrinsically electrically insulating, is provided with the background conductivity required for the (for example, electrochemical) generation of the free radical species or for the electrochemical detection of the radical-scavenged reaction product. The concentration of the electrolyte is chosen such that a sufficient level of background conductivity is established in the solution. The choice of electrolyte is determined by its solubility in the desired solvent and the electrochemical behaviour of the analyte of interest, e.g. the oxidation potential of the radical-scavenged form, see below. In addition, the selected electrolyte preferably should not (readily) react with the generated free radical species.

Preferred anions for the electrolyte are chloride, perchlorate and tetrafluoroborate. Other possible candidates include, but are not limited to, hexafluorophosphate, hexafluoroarsenate, trifluoromethanesolfonate, nitrate aromatic sulfonates and carboxylate. For the cation, tetraalkylammonium ions such as tetraethylammonium or tetrabutylammonium are preferred (although other tetraalkylammonium ions can also be used). Other candidate cations include, but are not limited to, Lithium, Sodium and Magnesium ions, as well as Sulfonium salts and Cryptates.

The extraction step can be tailored to remove species from the complex sample matrix that could interfere with the reaction between the analyte of interest and the free radical species. For instance, in the case of the analyte of interest being Propofol, the sample preparation/extraction step is tailored in such a way that the lifetime of the radical in the solution is sufficiently long to enable an accurate determination of the concentration of the analyte of interest, or more generally, to remove species that could interfere with the detection of the radical analyte reaction product or with the analyte radical reaction itself. Even if some of the radicals react with parts of the solution, this does typically not matter as the radical is generated in excess concentrations such that the loss of some of the radical through unintended reactions does not affect the concentration measurement.

The extract of the complex medium in the organic solvent, which contains the analyte of interest, is typically transferred to a radical reaction/analyte detection module. This step is not explicitly shown in FIG. 1. This module may be either separate from or connected directly to the SPE column via a fluid connection, and should provide an environment which is suitable for the reaction of free radicals with the analyte of interest. In a preferred embodiment, this module will also provide a means of detecting the radical-reacted product. However, the detection module can also be a separate entity from the radical reaction module, as will be explained in more detail with the aid of FIGS. 2 and 3 (vide infra).

After transfer of the extract into the radical reaction/analyte detection module, the method may proceed to optional step 140, in which a correlation or reference measurement may be performed. Such a measurement may for instance be useful if the crude extract of the complex medium contains substances that are likely to interfere with the measurement of the free radical-scavenged product. In such a case, a reference or calibration measurement can be taken in the absence of the free radical species. For example, in a preferred embodiment, which utilises electrochemical generation of superoxide radical anions, a positive potential voltammetry scan ranging from less negative potentials than the oxygen reduction potential to positive potentials above the superoxide-scavenged analyte oxidation potential can be performed before proceeding with steps 150, 160 and 170. The resulting signal can then be subtracted from the measurement obtained in step 170, as will be explained in more detail below.

It is preferred that step 140 forms part of the method of the present invention, as it ensures that a degree of selectivity for the analyte of interest is achieved in addition to the extraction described in step 120.

In step 150, the free oxygen radical species is generated and reacted with the lipophilic analyte molecule in step 160 to form the reaction product of the lipophilic analyte of interest and the free oxygen radical species, i.e. the radical-scavenged form of the analyte molecule. The free oxygen radical species may be generated in any suitable manner.

The primary aim is to generate free radical species which react with the analyte of interest, producing a product which is the radical-scavenged form of that analyte molecule. Possible methods of free radical generation, include, but are not limited to, chemical, electrochemical and enzymatic methods; these will be known to those skilled in the art. The optimal method will depend on the solvent system being employed, the free radical involved and the reactivity of the analyte of interest.

In a preferred embodiment, the superoxide radical anion ($O_2.^-$) is generated electrochemically. This may be achieved by holding the electrodes of a suitable electrochemical cell at a negative potential for a defined period of time. For example, a negative potential between −2V and −0.6V versus a standard calomel reference electrode may be used to reduce solvated molecular oxygen:

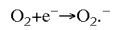

$$O_2 + e^- \rightarrow O_2.^-$$

Following the generation of this free oxygen radical species, the lipophilic analyte of interest will scavenge the electrochemically generated superoxide anion to create a more easily oxidizable species. The mechanism of superoxide scavenging depends on the nature of the analyte itself and on the solvent/electrolyte system employed. For example, $O_2.^-$ may act as an oxidant, reductant, base or nucleophile, as for instance is known from the textbook "Organic Chemistry" by H. Lund and O. Hammerich, CRC Press 2000.

In an alternative embodiment, the solvent/electrolyte system already may contains a source of $O_2.^-$, such as potassium superoxide (KO2). In this case, no electrochemical reduction of oxygen is required such that step 150 may be omitted and the detection of the superoxide-reacted analyte, i.e. step 170 may be performed immediately after the formation of the radical-scavenged form of the analyte molecule.

As mentioned above, the detection of the free radical-reacted analyte takes place in step 170 of the embodiment method of the present invention shown in FIG. 1. Usually, the product of free radical scavenging by the analyte molecule of interest has an enhanced detection signal relative to that associated with the unreacted analyte.

For example, when electrochemical detection is used, the free radical-scavenged analyte may have a lower oxidation potential and an enhanced electrochemical signal relative to that associated with the unreacted analyte. By monitoring the current signal at this potential, the presence and concentration of this free radical reacted product, and hence the presence and concentration of the original analyte in the sample, can be determined in step 180.

In the (electrochemical) measurement spectrum, the current peak at a particular voltage is typically associated with the presence of the reacted analyte of interest—radical complex. It cannot be ruled out that other peaks belonging to other species formed in side reactions are present in the electrochemical spectrum, but they can typically be distinguished from the reaction product of the analyte of interest because of their differing oxidation or reduction potentials. Therefore, as long as the reference measurement provides a reliable background measurement in the region of the peak in the electrochemical spectrum associated with the reacted analyte-of-interest—radical complex, an accurate determination of the concentration of the analyte of interest can be obtained.

In terms of the analyte of interest, the scavenged radical species typically oxidizes at a different, i.e. generally lower, potential than the unreacted species, such that the method of the present invention can be set up to ensure that the unreacted analyte of interest does either not react and does not contribute to the reference signal in the area at the voltages of interest, whilst the reacted species contributes to the measurement spectrum in this area at the voltages of interest. Such a set-up may for instance be achieved by suitable choice of the electrode voltages, sweep end points and/or voltages used for the analysis.

In a preferred embodiment, electrochemical methods, including, but not limited to, a potential sweep, e.g. a linear sweep, square wave, or differential pulse to increasingly positive values, or one or more potential steps to a value above the oxidation potential of the desired free radical-reacted analyte are used. However, it should be understood that depending on the properties of the species being detected, other detection techniques can be used, such as alternative electrochemical and/or optical detection techniques; such techniques will be apparent to those skilled in the art.

In addition, it should be understood that it is equally feasible to detect a reaction product by means of its electrochemical reduction rather than its electrochemical oxidation as mentioned above.

Figure 2:
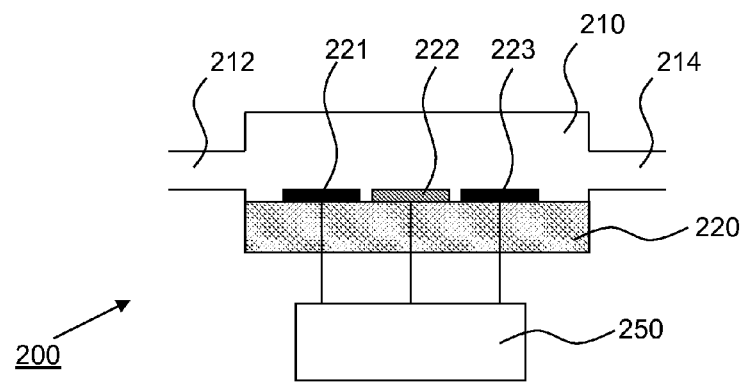

FIG. 2 schematically depicts a first embodiment of an apparatus 200 according to the present invention. The apparatus 200 comprises a plurality of electrodes 221-223 which are mounted on a carrier 220, which for instance may be a semiconductor substrate, an insulating substrate, such as a glass or plastic substrate, and so on. The electrodes 221-223 are located inside a first sample chamber 210 having an inlet 212 and an outlet 214. Alternatively, the inlet 212 may also be used as outlet, in which case outlet 214 may be omitted. The sample chamber 210 including electrodes 221-223 form a first electrochemical cell.

The electrodes 221-223 are conductively coupled to a controller 250 that is programmed to provide the electrodes with a plurality of voltages including at least one voltage above the oxidation potential of the radical-scavenged form of the analyte molecule, such that at that voltage, an electron is dislodged from the radical-scavenged form of the analyte molecule, which leads to the generation of a transient current. The intensity of this current is correlated to the concentration of the radical-scavenged form of the analyte molecule in the organic solvent, which concentration is correlated to the concentration of the lipophilic analyte of interest in the complex sample matrix. This transient current may be processed, e.g. measured, by a processor (not shown), which may be integrated in the controller 250 although this is not essential.

In a preferred embodiment, the controller 250 is also configured to implement step 140 of the method shown in FIG. 1, i.e. provide the electrodes 221-223 with a further plurality of voltages to perform a reference or calibration measurement to facilitate detection of the presence of interfering species in the organic solvent. In this embodiment, the signal processor may be adapted to measure the signals, e.g. transient currents generated during this calibration step, and may be further adapted to determine, e.g. measure the concentration of the lipophilic analyte of interest from the difference between the signal generated by said electrodes during the oxidation of the radical-scavenged form of the analyte molecule and the signal generated by said electrodes during the calibration measurement. To this end, the signal processor may for instance comprise a memory to store the calibration or reference measurement and the actual measurement results for generating the differential signal in a post-processing step.

The electrochemical cell in FIG. 2 formed by the sample chamber 210 and the electrodes 221-223 may also be used to generate the free oxygen radical species, if not already present in the organic solvent. One example of an integrated radical generation and radical-scavenged analyte detection module includes, but is not limited to, a three electrode electrochemical cell, consisting of platinum working and counter electrodes and a silver/silver ion (Ag/Ag$^+$) pseudo reference electrode. However, it should be understood that other electrode configurations are equally suitable. Depending on the solvent and electrolyte system being employed, other candidate reference electrodes include, but are not limited to, saturated calomel electrodes (SCE), silver/silver chloride (Ag$^+$/AgCl), and triiodide/iodide electrodes (Pt/I$_3^-$/I$^-$). Preferred working electrode candidates include, but are not limited to, gold, silver, platinum, other metals and carbon. The controller 250 may further be configured to provide a constant negative voltage across the electrodes 221-223 for a defined period of time to generate the radical species.

Figure 3:
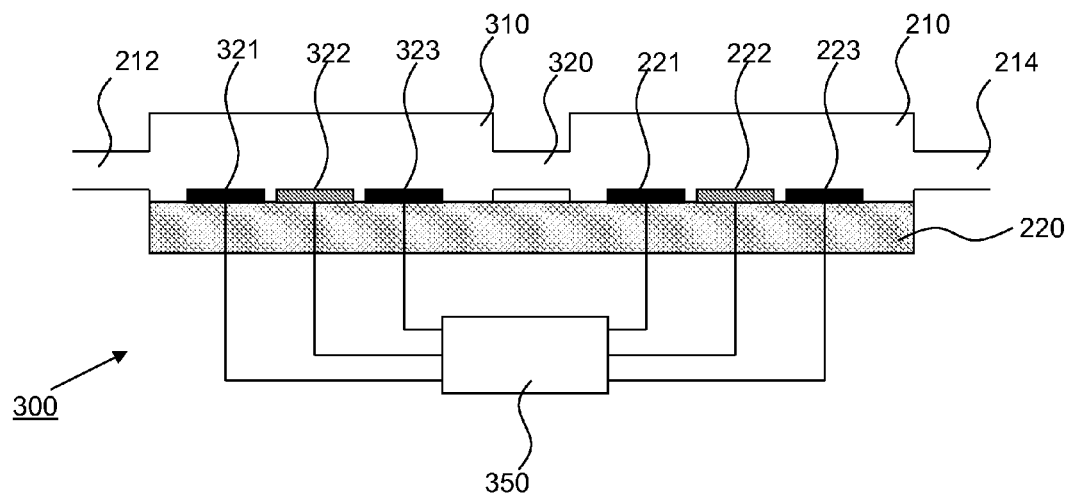

It is, however, not necessary that the free radical species generation and the radical-scavenged analyte detection take place in the same electrochemical cell. FIG. 3 depicts an embodiment of an apparatus 300, in which a second electrochemical cell defined by a second sample chamber 310 comprising further electrodes 321-323 is present to generate the free radical species, with the first electrochemical cell formed by sample chamber 210 and electrodes 221-223 configured to perform the radical scavenged analyte detection. The electrochemical cells are in fluid communication with each other via a fluidic connector 320, e.g. a tube.

The controller 350 may be configured in the same manner as controller 250, with the difference being that controller 350 is adapted to provide the further electrodes 321-323 (i.e. electrodes 321, 322 and 323) with the constant voltage signal for the generation of the free radical species, and is further adapted to provide the electrodes 221-223 (i.e. electrodes 221, 222 and 223) with the voltage sweep(s) to perform the radical scavenged analyte detection and the calibration measurement, if applicable.

In FIG. 3, the electrodes 221-223 and further electrodes 321-323 are carried by the same carrier 220 by way of non-limiting example only. It should be understood that the electrodes 221-223 and further electrodes 321-323 may equally be mounted on separate carriers. In yet another embodiment (not shown), the different electrochemical cells are not in fluidic communication with each other, in which case the sample comprising the generated radical-scavenged analyte, which forms as soon as the free radical species has been generated, is transferred from one cell to the other by a separate transport device and/or container. Further variations to the apparatus 200 or 300 will be apparent to the skilled person.

The present invention will now be illustrated in more detail by the following examples. It should be understood that these examples have been chosen for illustrative purposes only and are not intended to define or limit the scope of the present invention.

Example 1

In this example, the anaesthetic drug Propofol is detected from whole blood using solid phase extraction (SPE) followed by cyclic voltammetry (electrochemical) detection of the superoxide-reacted drug. Existing Propofol detection technologies rely on time-consuming HPLC techniques. The low complexity and cost of the technique described in this example enables a Propofol assay that can be performed in a near-patient setting.

A blood sample (preferably 1 ml), which contains Propofol, is diluted 1:2 into water and then the entire sample is applied to a 30 mg Strata™-x SPE column. The column is washed with (preferably 2 ml) of a 1:1 mixture of water and methanol to remove weakly bound impurities. The Propofol is then eluted from the SPE column using a known volume (preferably 0.5 ml) of acetonitrile containing 0.1M tetraethylammonium chloride. The solid phase extraction of Propofol into acetonitrile has been detailed elsewhere; see L. McGaughran, L. J. Voss, R. Oliver, M. Petcu, P. Schaare, J. P. M. Barnard, and J. W. Sleigh, "Rapid measurement of blood Propofol levels: A proof of concept study," Journal of Clinical Monitoring and Computing, vol. 20, 2006, pp. 381-381.

Figure 4:
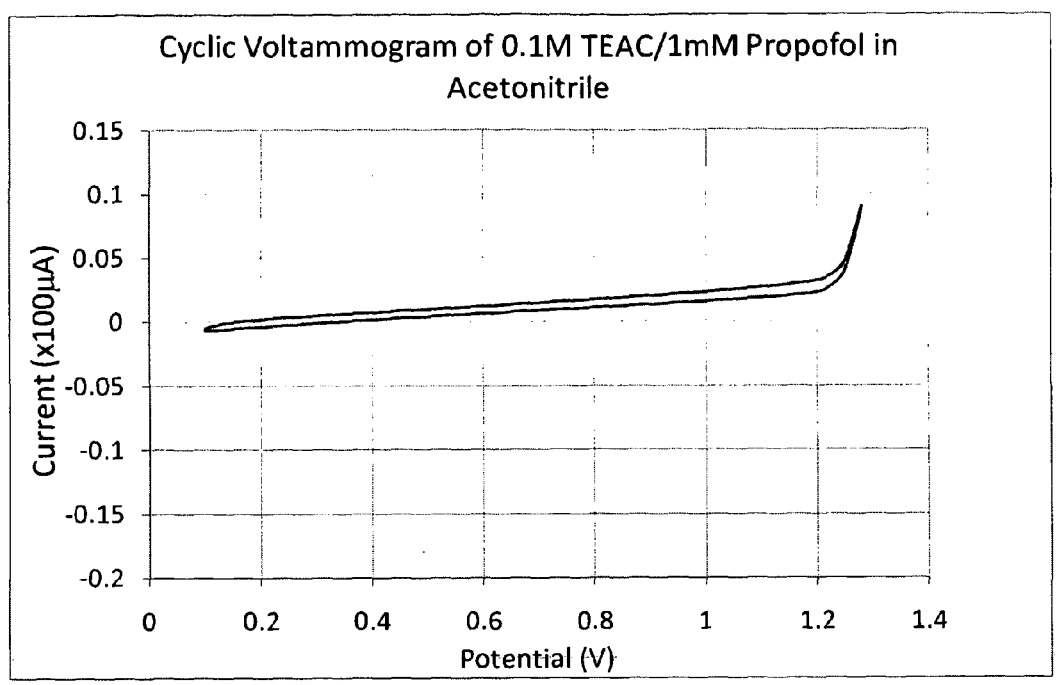
FIG. 4 depicts a negative control trace of 0.1 mM Propofol and 0.1 mM tetraethylammonium chloride (TEAC) in acetonitrile (MeCN) as obtained by cyclic voltammetry.

The eluent is subsequently transferred to an electrochemical measurement cell comprising a platinum working electrode, a platinum counter electrode and an Ag/Ag$^+$ pseudo-reference electrode. Cyclic voltammetry is used to measure the Propofol concentration in the extract. First, impurities are detected using a potential sweep from 100 mV to 800 mV. Propofol does not oxidise in this potential window and the superoxide-scavenged Propofol product is not present as the free radical species has not yet been generated. The resulting plot, which is shown in FIG. 4, therefore serves as the "negative control trace".

Next, the potential is held at −1V for a defined period of time, preferably between 10 and 60 seconds, to reduce the dissolved oxygen to $O_2.^-$. Propofol is known to have a powerful free radical scavenging activity, as for instance has been disclosed by: Gülcin, H. A. Alici, and M. Cesur, "Determination of in vitro antioxidant and radical scavenging activities of Propofol," Chemical & pharmaceutical bulletin, Vol. 53, 2005, pp. 281-285, G. L. Volti, P. Murabito, G. Attaguile, L. F. Rodella, M. Astuto, C. Di Giacomo, and A. Gullo, "Antioxidant properties of Propofol when oxidative stress sleeps with patients. Excli J. 2006; 5: 25-32," Links. Consequently, the electrochemically generated $O_2.^-$ therefore reacts readily with the drug.

Figure 5:
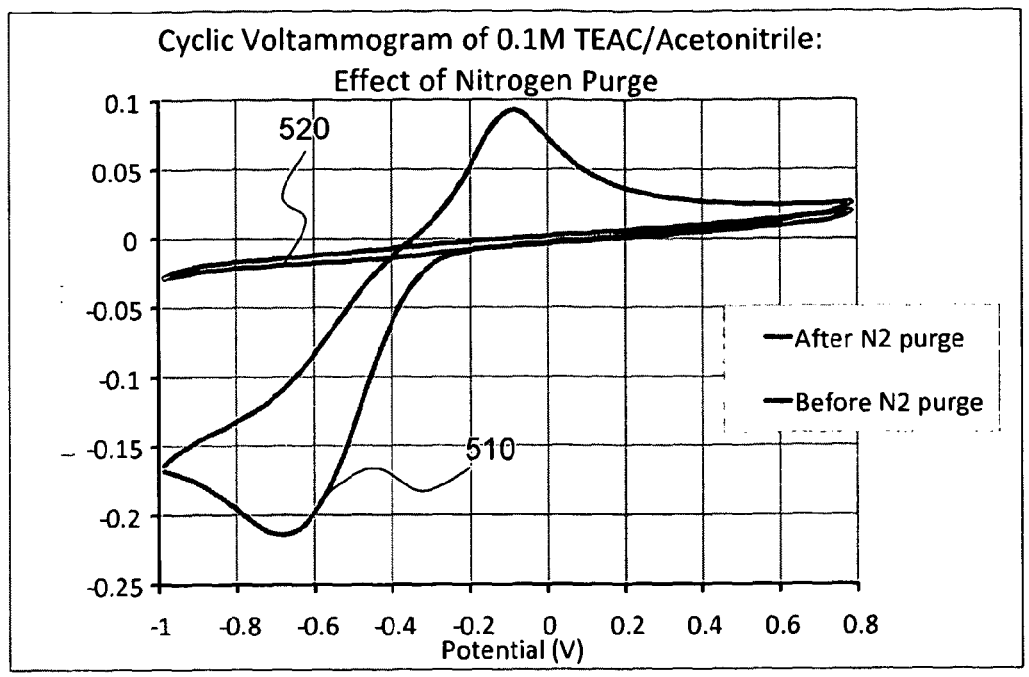
FIG. 5 depicts a cyclic voltammetry plot of 0.1 mM TEAC in MeCN before and after nitrogen purse in the presence of Propofol.

The electrode potential is then swept to +0.8V and an oxidation peak is observed at around 350 mV, as shown in FIG. 5. This peak is attributed to the superoxide-scavenged form of Propofol. Subtraction of the "negative control trace" from the measurement trace removes any impurity signals. Comparison of the peak current value of the subtracted trace at 350 mM with a calibration plot of known Propofol concentrations in the solvent yields the unknown concentration.

Alternatively, the area of this same peak on a current versus potential plot can be used to generate the response versus Propofol concentration calibration plot. In a similar way, this calibration plot can be compared with the peak area generated by a sample with an unknown amount of Propofol to determine the concentration of the molecule in this sample.

Depending on the solvent system used, different reaction pathways will occur to generate the superoxide-scavenged Propofol (R—OH) product, as for instance is known from P. G. Murphy, D. S. Myers, M. J. Davies, N. R. Webster, and J. G. Jones, "The Antioxidant Potential of Propofol (2,6-diisopropylphenol)," Br. J. Anaesth., vol. 68, June 1992, pp. 613-618 and D. Hauchard, C. Lagrost, and P. Hapiot, "Superoxide Protonation by Weak Acids in Imidazolium Based Ionic Liquids," The Journal of Physical Chemistry B, vol. 113, March 2009, pp. 2826-2831.

Examples of these reactions include, but are not necessarily limited to, the following two reactions:

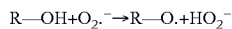

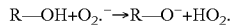

In the first reaction, Propofol (R—OH) scavenges the free radical by a process of hydrogen abstraction from the phenolic hydroxyl group of the drug to give a phenoxy radical. In the second reaction, the superoxide anion acts as an electrogenerated base, producing a phenolate anion.

Figure 6:
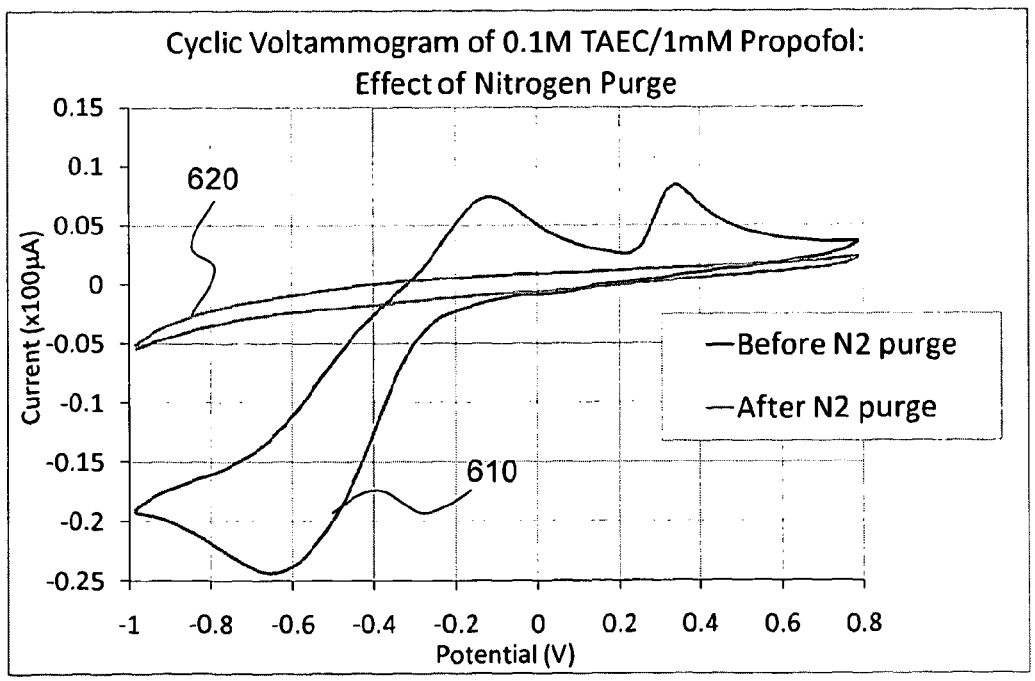
FIG. 6 depicts a cyclic voltammetry plot of 0.1 mM TEAC in MeCN before and after nitrogen purse in the absence of Propofol.

As shown in FIG. 5 and FIG. 6, the superoxide-scavenged Propofol species (either the phenoxyradical or the phenolate anion) is readily oxidizable during the potential sweep from −1V to 0.8V. FIG. 5 shows the $O_2/O_2.^-$ redox pair during a cyclic voltammetry (CV) sweep from −1V to 0.8V to −1V (trace 510). $O_2$ is reduced at −600 mV and the $O_2.^-$ is re-oxidised to $O_2$ at −120 mV. A nitrogen purge (trace 520), which removes the dissolved oxygen from the solution, attenuates the peaks. This confirms that the origin of the redox pair is indeed dissolved oxygen. FIG. 6 shows the same measurements in the presence of Propofol. Note the appearance of another irreversible oxidation peak in trace 610 at 350 mV, which is attributed to superoxide-scavenged Propofol. A nitrogen purge (trace 620) attenuates all the peaks, confirming that the peak at 350 mV is indeed a product of $O_2.^-$ scavenging by Propofol. A "negative control" scan from 100 mV to 800 mV is shown in FIG. 4, and confirms that Propofol cannot be detected at these low potentials in the absence of superoxide. This example demonstrates that this method can be used to enhance the electrochemical signal of an analyte such as a lipophilic analyte by reacting it with a radical species.

Example 2

In this example, the anaesthetic drug Propofol is detected in a sample using square wave voltammetry instead of cyclic voltammetry as described in example 1 to detect the superoxide-reacted drug. A (preferably 1 ml) sample containing Propofol is applied to a 30 mg Strata™-x SPE column. The column is washed with (preferably 2 ml) of a 1:1 mixture of water and methanol to remove weakly bound impurities. The Propofol is then eluted from the SPE column using a known volume (preferably 0.5 ml) of acetonitrile containing 0.1 M TEAC.

The eluent is then transferred to the electrochemical reaction cell described in example 1 (platinum working electrode, a platinum counter electrode and an Ag/Ag+ pseudo-reference electrode). Square wave voltammetry is used to detect the superoxide-scavenged drug. This technique is well known to those skilled in the art, and for this reason it will not be described here in detail. For each sample, the system is held at a potential of −1V for 30 seconds to reduce the molecular oxygen to the superoxide radical anion ($O_2.^-$), before being swept to a potential of +800 mV using a square wave amplitude of 25 mV, a frequency of 8 Hz and a potential step of 10 mV. As no impurities are present in these particular solutions, a "negative control" scan in the absence of superoxide is not taken. As in the previous example, the superoxide-reacted Propofol species is detected at a potential of ~350 mV.

Figure 7:
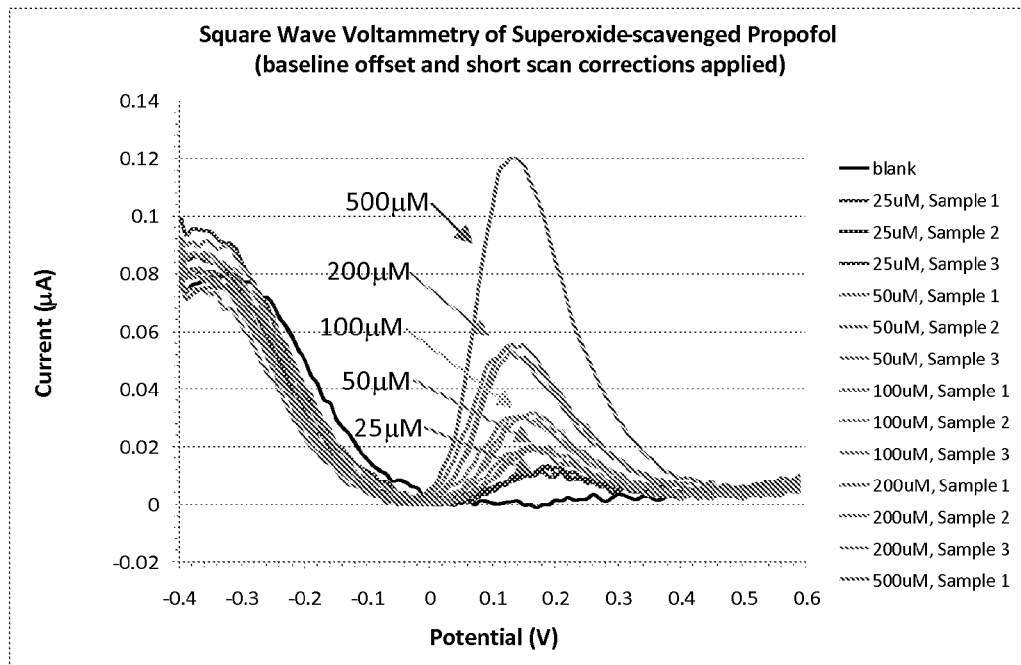
FIG. 7 depicts a square wave voltammetry plot of a series of Propofol concentrations measured with the method of the present invention.
Figure 8:
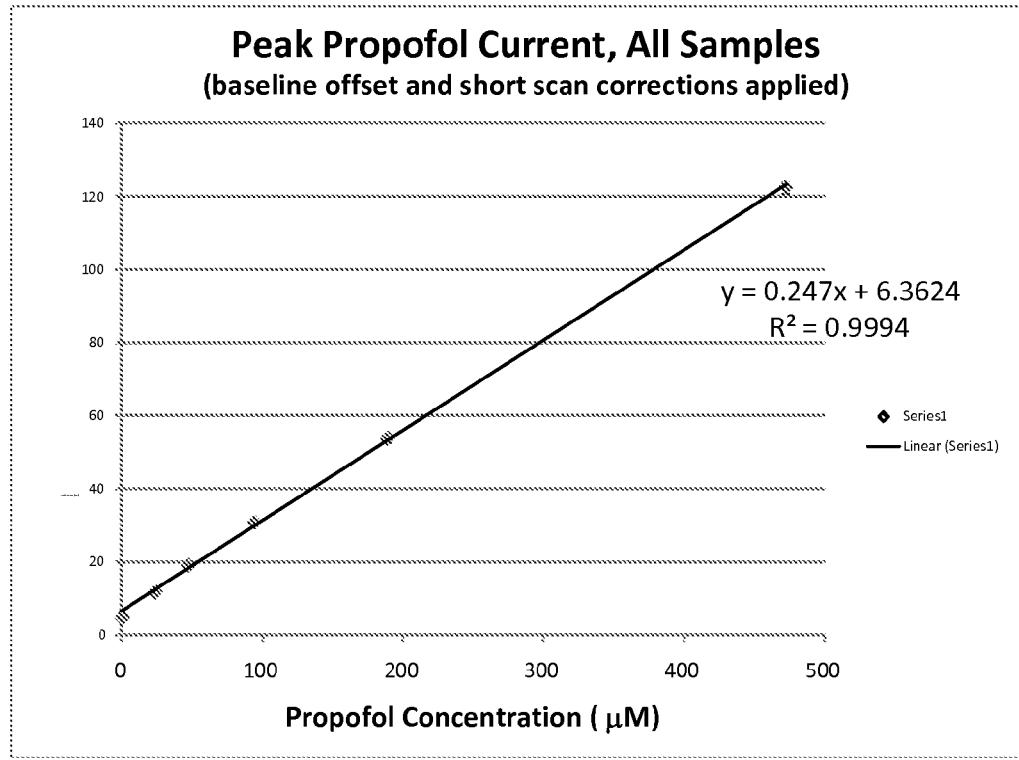
FIG. 8 depicts a plot of the Propofol concentrations extracted from the measurements depicted in FIG. 7.

The maximum current and area of this peak is baseline-corrected and recorded. Then, this sample is removed from the reaction cell and another sample measured in the same way. The utility of this example method for determining unknown Propofol concentrations in a sample is demonstrated in FIG. 7 and FIG. 8. The concentration dependence of the superoxide-scavenged Propofol peak current as measured by square wave voltammetry is shown in FIG. 7, while the resulting calibration plot of the baseline-corrected peak current is shown in FIG. 8. A clear linear dependence is observed with Propofol concentration in the acetonitrile eluent between 30 mM and 250 mM. This demonstrates that this measurement technique produces a signal that varies with the drug concentration in a predictable manner. It can therefore be applied to determine unknown concentrations of the drug.

In summary, the method and apparatus of the present invention have several advantages over the prior art. Firstly, the required sample preparation to extract the analyte of interest from the complex sample matrix is simpler than that demanded for techniques such as HPLC, resulting in substantial savings in equipment complexity, financial cost and time of measurement.

Also, the use of an electrochemical concentration measurement method instead of an optical method provides a route to miniaturisation.

Furthermore, the usual problems associated with electrode fouling by adsorbed hydrophobic materials from the complex sample matrix are also avoided by exchange into an organic solvent.

In addition, the free radical-reacted analyte is much more readily oxidised at lower potentials relative to the unreacted analyte. Therefore, the chance of interference by other oxidisable species is reduced by using lower detection potentials.

Another significant advantage over the prior art is provided in the embodiment of the method of the present invention in which a negative control measurement is performed in the absence of free radicals (step 140). This enhances the selectivity for the analyte of interest by measuring the signal from species that would otherwise interfere with the measurement at the same potential.

Finally, there is a significant improvement over the prior art for the detection of phenols. In the present invention, the conversion to a free radical-reacted product with different electrochemical properties avoids the problem of phenol radical polymerisation and electrode passivation that is normally associated with conventional electrochemical detection. For example, passivation does not occur when superoxide-reacted phenols are oxidised electrochemically and hence no loss of sensitivity occurs with repeated measurement, as demonstrated in the examples above.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. A method for detecting the concentration of a lipophilic analyte of interest in a complex sample matrix, the method comprising:
    extracting an analyte of interest from said sample into an organic solvent comprising a dissolved electrolyte;
    providing a free radical species in said organic solvent by holding the organic solvent at a predefined potential for a predefined period of time;
    reacting the analyte of interest with said free radical species; and
    performing a measurement to detect the concentration of the free radical-reacted analyte reaction product.

2. The method of claim 1, wherein the free radical species is a free oxygen radical species.

3. The method of claim 1, wherein the organic solvent further comprises a free oxygen radical precursor, and wherein the step of providing the free radical species comprises generating said species from the oxygen radical precursor.

4. The method of claim 2, wherein the free oxygen radical precursor is comprised by the dissolved electrolyte.

5. The method of claim 1, further comprising:
    performing a reference measurement prior to said generation step; and
    detecting the concentration of the lipophilic analyte of interest by subtracting the reference measurement from the measurement.

6. The method of claim 1, wherein the method further comprises transferring the organic solvent comprising the free radical-reacted analyte reaction product to an analysis unit prior to performing said measurement.

7. The method of claim 1, wherein the organic solvent is an aprotic solvent selected from the group consisting of dimethylformamide, acetonitrile and dimethylsulfoxide.

8. The method of claim 1, wherein the electrolyte cation is selected from the group consisting of a tetra-alkyl ammonium, lithium, sodium, magnesium, sulfonium and cryptate cations.

9. The method of claim 1, wherein the electrolyte anion is selected from the group consisting of chloride, perchlorate, tetrafluoroborate, hexafluorophosphate, hexafluoroarsenate, trifluoromethanesulfonate, nitrate, aromatic sulfonates and carboxylate anions.

10. The method of claim 1, wherein the measurement is an electrochemical measurement comprising a potential sweep, said sweep including at least one voltage value exceeding the oxidation or reduction potential of the free radical-reacted analyte reaction product.

11. The method of claim 1, wherein the analyte of interest is Propofol.

12. An apparatus for detecting the concentration of a lipophilic analyte of interest, comprising:
    an electrochemical cell for performing a measurement to detect the concentration of a radical-reacted analyte reaction product of a free radical species and an analyte of interest in an organic solvent further comprising an electrolyte dissolved therein, said electrochemical cell comprising a plurality of electrodes;
    a controller programmed to provide said electrodes with a plurality of voltages including at least one voltage value exceeding the oxidation or reduction potential of the free radical-reacted analyte reaction product, said controller being further adapted to generate a constant voltage signal over a predetermined time period for generating the free radical species; and
    a signal processor coupled to said electrodes for determining the concentration of the analyte of interest from the signal generated by said electrodes in response to said plurality of voltages.

13. The apparatus of claim 12, wherein the controller is further programmed to provide said electrodes with a further plurality of voltages defining a reference measurement for detecting the presence of interfering species in the organic solvent, and wherein the signal processor is adapted to determine the concentration of the analyte of interest from the difference between the signal generated by said electrodes in response to said plurality of voltages and the signal generated by said electrodes in response to said further plurality of voltages.

14. The apparatus of claim 12, wherein the free radical species is a free oxygen radical species.

\* \* \* \* \*